United States Patent [19]  
Yamane et al.

[11] Patent Number: 4,983,602  
[45] Date of Patent: * Jan. 8, 1991

[54] 3'-HYDROXYBENZOXAZINORIFAMYCIN DERIVATIVE, PROCESS FOR PREPARING THE SAME AND ANTIBACTERIAL AGENT CONTAINING THE SAME

[75] Inventors: Takehiko Yamane, Akashi; Takuji Hashizume, Takasago; Katsuji Yamashita, Kobe; Kazunori Hosoe, Takasago; Fumiyuki Kuze, Kyoto; Kiyoshi Watanabe, Akashi, all of Japan

[73] Assignee: Kanegafuchi Kagaku Kogyo Kabushiki Kaisha, Osaka, Japan

[*] Notice: The portion of the term of this patent subsequent to Sep. 1, 2004 has been disclaimed.

[21] Appl. No.: 407,995  
[22] Filed: Sep. 14, 1989  
[30] Foreign Application Priority Data Nov. 1, 1988 [JP] Japan ................................. 63-276661  
Mar. 30, 1989 [JP] Japan ..................................... 1-80396

[51] Int. Cl.$^5$ .................. C07D 498/16; A61K 31/535  
[52] U.S. Cl. .................................. 514/229.5; 540/457  
[58] Field of Search .............. 540/457; 514/185, 229.5

[56] References Cited  
U.S. PATENT DOCUMENTS 3,338,888 8/1967 Bickel et al. .  
4,005,077 1/1977 Bickel et al. .  
4,690,919 9/1987 Yamane et al. .  
4,859,661 8/1989 Kano et al. .

FOREIGN PATENT DOCUMENTS 0190709 8/1986 European Pat. Off. .  
59-231092 12/1984 Japan .  
1081757 8/1967 United Kingdom .

OTHER PUBLICATIONS

Noller "Chemistry of Organic Compounds", Second Edition (1987) (Saunders), p. 170.  
Chemical Abstracts, vol. 68, No. 23, Jun. 1968, Abstract No. 104800f.  
Chemical Abstracts, vol. 68, Subject Index E-O, Jan.-Jun. 1968, p. 13835, column 3, formula 1, keyword "2,7-(Epoxypentadeca[1,11,13]-trienimino)-6H-benzofuro[4,5-a]phenoxazine-1,6,15(2H)-trione".

Primary Examiner—Mukund J. Shah  
Assistant Examiner—E. C. Ward  
Attorney, Agent, or Firm—Armstrong, Nikaido, Marmelstein, Kubovcik & Murray

ABSTRACT

A rifamycin derivative having the formula (I):

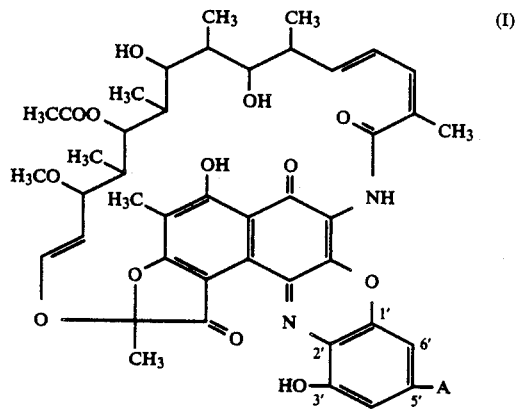

wherein A is a group having the formula:

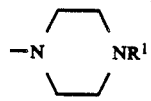

in which $R^1$ is an alkyl group having 4 or 5 carbon atoms or an alkenyl group having 3 to 5 carbon atoms, or a group having the formula:

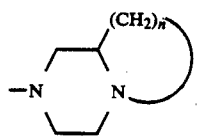

in which n is 3 or 4; or a pharmaceutically acceptable salt thereof. The rifamycin derivative (I) exhibits a strong antibacterial activity against Gram-positive bacteria and acid-fast bacteria, and also exhibits a strong antibacterial activity against tubercle bacilli.

9 Claims, 1 Drawing Sheet

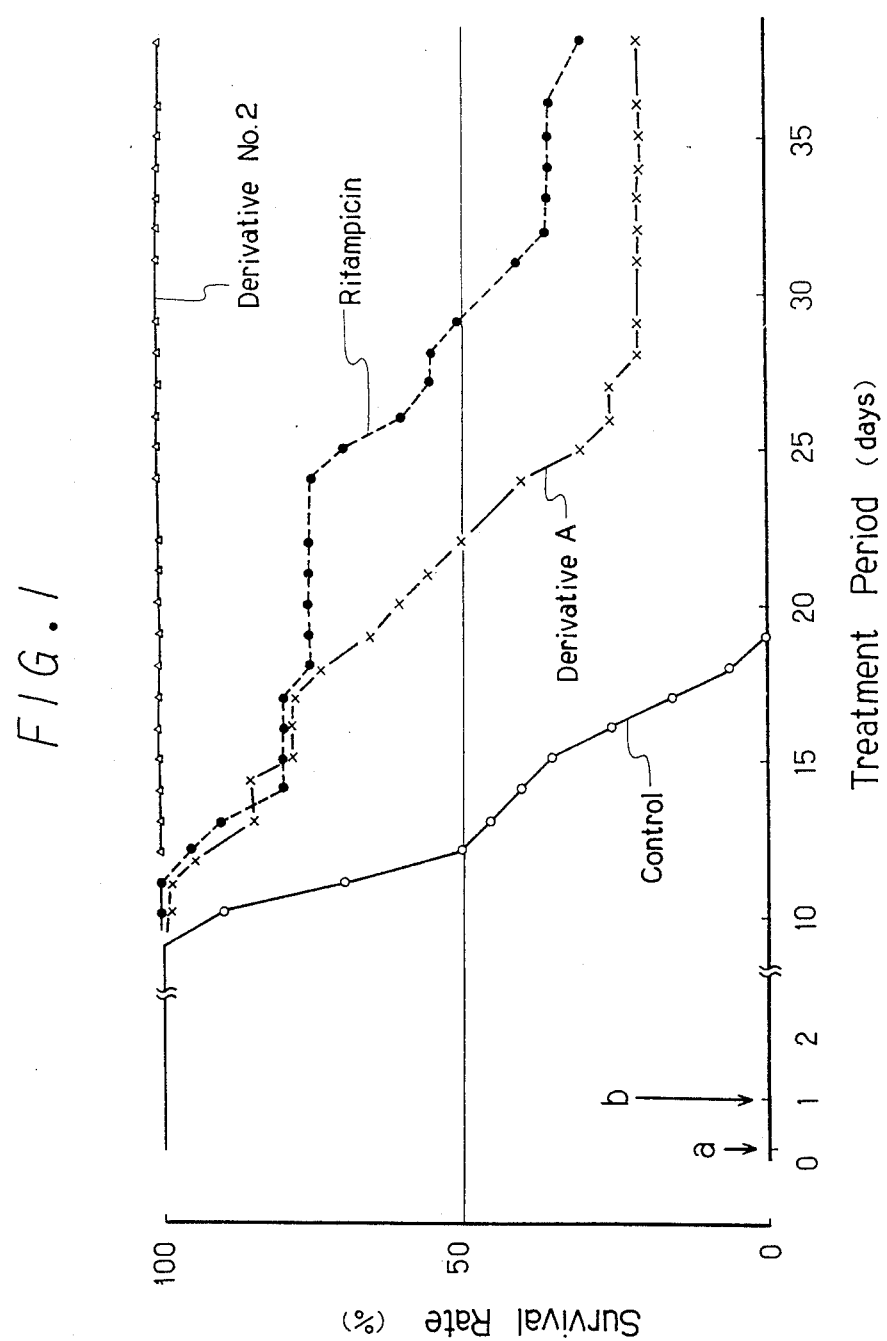

3'-HYDROXYBENZOXAZINORIFAMYCIN DERIVATIVE, PROCESS FOR PREPARING THE SAME AND ANTIBACTERIAL AGENT CONTAINING THE SAME

BACKGROUND OF THE INVENTION

The present invention relates to a novel rifamycin derivative or salts thereof, a process for preparing the same and antibacterial agents containing the same as an effective ingredient. More particularly, the present invention relates to a novel rifamycin derivative having the formula (I):

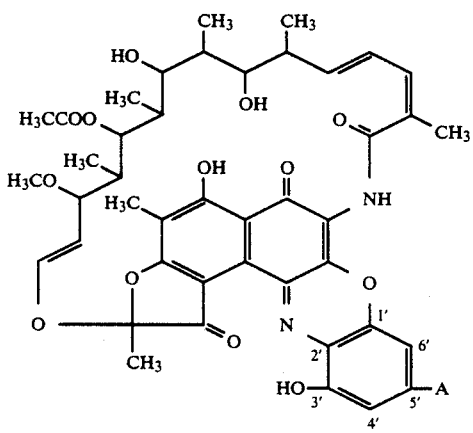

wherein A is a group having the formula:

in which $R^1$ is an alkyl group having 4 or 5 carbon atoms or an alkenyl group having 3 to 5 carbon atoms, or a group having the formula:

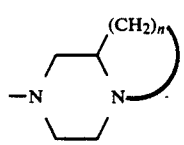

in which n is 3 or 4; or a salt thereof, a process for preparing the same and antibacterial agents containing the rifamycin derivative or a pharmaceutically acceptable salt thereof as an effective ingredient.

The rifamycin derivative of the present invention is a novel compound which has not yet been reported in the literature.

For the purpose of developing a novel superior antibacterial agent, the present inventors have synthesized a novel rifamycin derivative having the formula (I):

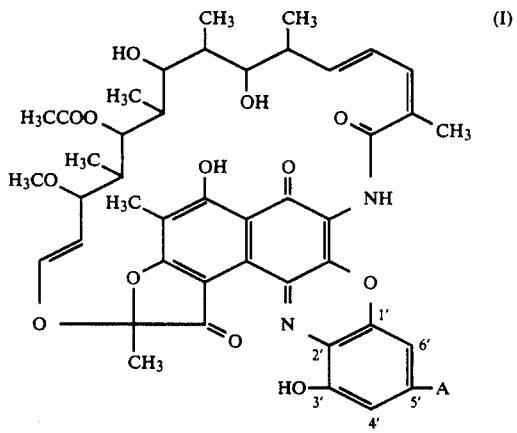

wherein A is as defined above and investigated the antibacterial activity and pharmacological characteristics thereof, and as a result, found that the novel rifamycin derivative having the formula (I) exhibits a strong antibacterial activity and excellent pharmacological characteristics.

SUMMARY OF THE INVENTION

The present invention provides a novel rifamycin derivative having the formula (I):

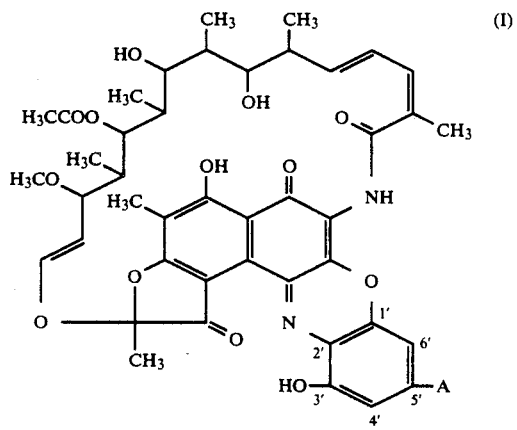

wherein A is a group having the formula:

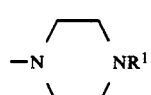

in which
$R^1$ is an alkyl group having 4 or 5 carbon atoms or an alkenyl group having 3 to 5 carbon atoms, or a group having the formula:

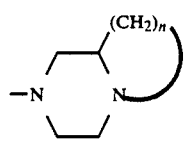

in which n is 3 or 4;
or a salt thereof.

Further, the present invention provides a procses for preparing the rifamycin derivative having the formula (I) or a salt thereof, which comprises reacting a rifamycin derivative having the formula (II):

$$\text{(II)}$$

with an amine having the formula:

A—H wherein A is as defined above.

Still further, the present invention provides an antibacterial composition comprising the rifamycin derivatives having the formula (I) or a pharmaceutically acceptable salt thereof as an effective ingredient.

BRIEF EXPLANATION OF THE DRAWING

FIG. 1 is a graph showing relationships between the survival rate of mice and the treatment period in tests wherein the rifamycin derivative of the invention or other test compounds were orally administered to mice suffering from tuberculosis.

DETAILED DESCRIPTION

The rifamycin derivative having the formula (I) according to the present invention is soluble in various kinds of organic solvents, e.g. halogenated hydrocarbons such as chloroform, alcohols such as ethanol, esters such as ethyl acetate, aromatic hydrocarbons such as benzene, and ethers such as tetrahydrofuran.

Examples of the substituent, A, in the novel rifamycin derivative (I) of the present invention are as follows:

Examples of the group:

$$-N\diagdown NR^1$$

in which $R^1$ is as defined above, for A are, for instance,

—N⟩N-CH₂CH₂CH₂CH₃, —N⟩N-CH₂CH(CH₃)₂,

—N⟩N-C(CH₃)₃, —N⟩N-CHCH₂CH₃ | CH₃

—N⟩N-(CH₂)₄CH₃, —N⟩N-CH₂CH₂CH(CH₃)₂,

—N⟩N-CH₂-△, —N⟩N-CH₂-▱,

—N⟩N-CH₂CH=CH₂, —N⟩N-CH₂CH=CHCH₃,

—N⟩N-CH₂CH₂CH=CH₂,

—N⟩N-CH₂CH=C(CH₃)₂,

—N⟩N-CH₂C(CH₃)=CH₂, and the like.

Examples of the group:

$$-N\diagdown N{-}(CH_2)_n$$

in which n as defined above, for A are and

The rifamycin derivative (I) of the present invention can form a salt with either a base or an acid. Any base or acid capable of forming a salt with the rifamycin derivative (I) can be employed. Examples of the salts with bases are (1) metal salts, especially alkali metal salts and alkaline earth metal salts, (2) ammonium salt, and (3) amine salts, especially salts with methylamine, ethylamine, diethylamine, triethylamine, pyrrolidine, morpholine or hexamethyleneimine, or the like. Examples of the salts with acids are (1) salts with mineral acids such as sulfuric acid and hydrochloric acid, and (2) salts with organic acids such as ptoluenesulfonic acid, trifluoroacetic acid and acetic acid.

The rifamycin derivative of the present invention having the formula (I) can be prepared by the following processes:

(A) The rifamycin derivative (I) can be prepared by reacting 3'-hydroxybenzoxazinorifamycin having the formula (II):

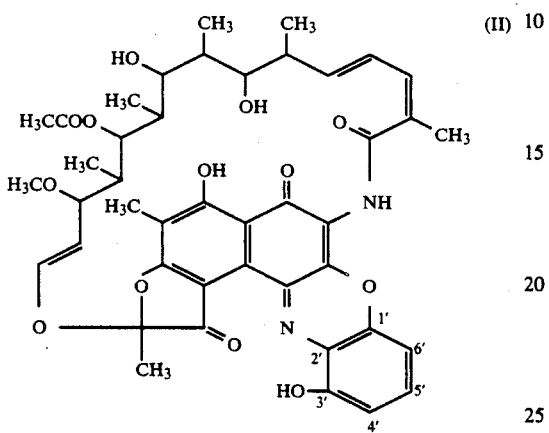

which is prepared according to the process described in USP 4,690,919, dissolved in an organic solvent such as methanol, ethanol, tetrahydrofuran, N,N-dimethylformamide or dimethyl sulfoxide, with an amine having the formula:

A—H wherein A is as defined above, in the presence or absence of an acid such as hydrochloric acid at a temperature ranging from −20° C. to the boiling point of the solvent used for 1 hour to 1 month and in the presence or absence of an oxidizing agent such as manganese dioxide.

In the above reaction, the amine having the formula: A—H wherein A is as defined above, is used in an amount of 0.5 to 10 moles, preferably 1 to 3 moles per 1 mole of the rifamycin derivative having the formula (II), yielding more favorable results.

Examples of the reaction solvent employed in the above process are, for instance, methanol, ethanol, isopropyl alcohol, tetrahydrofuran, pyridine, acetone, ethyl acetate, chloroform, N,N-dimethylformamide, dimethylsulfoxide, and the like. Among them, pyridine, N,N-dimethylformamide and dimethylsulfoxide are preferably employed with more favorable results.

The reaction temperature ranges from −20° C. to the boiling point of the solvent used, and the preferred reaction temperature ranges from −5° C. to 50° C., yielding more favorable results.

The reaction time usually ranges from 1 hour to 1 month. However, the optimum reaction time should be determined by following the progress of the reaction by means of thin layer chromatography or the like since the reaction time varies depending on reaction conditions such as the kind and amount of the amine employed, the presence or absence of an oxidizing agent, the kind and amount of the oxidizing agent employed, and the reaction temperature.

When the reaction is carried out in the presence of an oxidizing agent, air, oxygen, manganese dioxide, lead dioxide, silver oxide, potassium ferricyanide, hydrogen peroxide, and the like are employed as the oxidizing agent. Among them, manganese dioxide, silver oxide and potassium ferricyanide are preferably employed with more favorable results.

(B) The rifamycin derivative (I) can be prepared according to the above-mentioned process (A) using a rifamycin derivative having the formula (III):

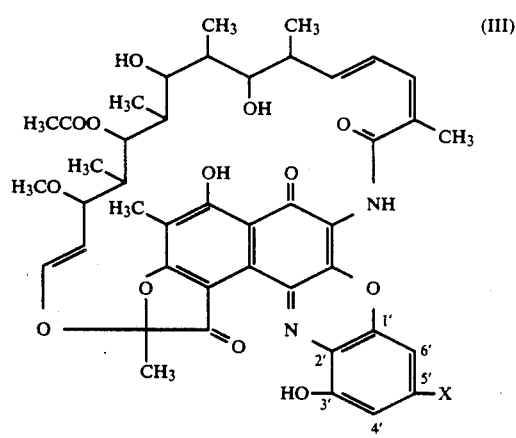

wherein X is a halogen atom, an alkoxyl group having 1 to 6 carbon atoms or nitro group, instead of the rifamycin derivative having the formula (II) used in the process (A). The reaction conditions, e.g. reaction solvent, reaction temperature, and the like, may be the same as those described in the process (A).

The rifamycin derivative having the formula (III), which is a starting material in the process of the invention, can be prepared by reacting rifamycin S with a compound represented by the formula:

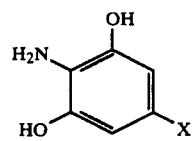

wherein X is as defined above, according to the process for preparing 3'-hydroxybenzoxazinorifamycin disclosed in U.S. Pat. No. 4,690,919.

The rifamycin derivative (I) according to the present invention, which is a dark violet solid, can be isolated and purified from the reaction mixture in a relatively easy manner. That is, an excess amount of the amine having the formula: A—H wherein A is as defined above and the reaction solvent, etc, are removed from the reaction mixture to give a crude product, which is then purified by crystallization, column-chromatography or the like. Thus, the desired rifamycin derivative can be obtained.

The rifamycin derivative (I) of the present invention can be converted into a rifamycin derivative having the formula (IV):

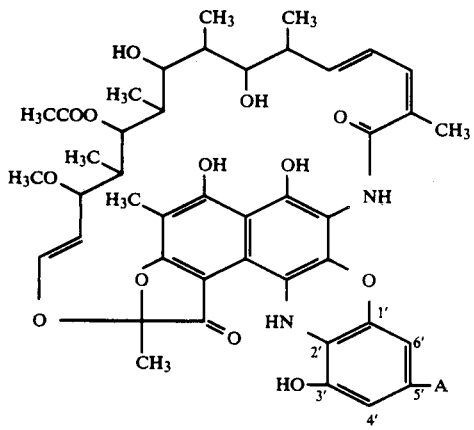

(IV)

wherein A is as defined above, by reducing the rifamycin derivative (I) with a reducing agent such as ascorbic acid or sodium hydrosulfite. The rifamycin derivative having the formula (IV) is also a novel compound and possesses a strong antibacterial activity.

Typical examples of the rifamycin derivatives (I) of the present invention are shown in Table 1. The infrared absorption (IR) spectrum was measured according to the potassium bromide tablet method. The thin layer chromatography (TLC) was carried out using silica gel 60 $F_{254}$ plate for thin layer chromatography (20 cm × 20 cm, E. Merck Co.). The nuclear magnetic resonance (NMR) spectrum was measured in deuterated chloroform using tetramethylsilane as an internal standard.

TABLE 1

| Derivative No. | A | Crystal form | TLC Rf | TLC Solvent system* | IR spectrum (cm$^{-1}$) | Chemical shift of proton in amino group introduced** (δ, ppm) |
|---|---|---|---|---|---|---|
| 1 | —N⟨⟩NCH$_2$CH$_2$CH$_2$CH$_3$ | plate | 0.34 | A | 1613 (C=O) | 3.70 (C$\underline{H}_2$NC$\underline{H}_2$, 4H, br) |
| 2 | —N⟨⟩NCH$_2$CH(CH$_3$)$_2$ | prism | 0.55 | C | 1615 (C=O) | 3.60 (C$\underline{H}_2$NC$\underline{H}_2$, 4H, br) |
| 3 | —N⟨⟩NCH$_2$—◁ | amorphous | 0.58 | B | 1610 (C=O) | 0.13, 0.50 (CH⟨CH$_2$/CH$_2$⟩, 4H, br) |
| 4 | —N⟨⟩NCH⟨CH$_3$/C$_2$H$_5$⟩ | amorphous | 0.63 | D | 1618 (C=O) | 3.63 (C$\underline{H}_2$NC$\underline{H}_2$, 4H, br) |
| 5 | —N⟨⟩NCH$_2$CH$_2$CH(CH$_3$)$_2$ | plate | 0.62 | B | 1620 (C=O) | 3.65 (C$\underline{H}_2$NC$\underline{H}_2$, 4H, br) |
| 6 | —N⟨⟩NC(CH$_3$)$_3$ | flake | 0.16 | D | 1606 (C=O) | 1.06 (C$\underline{H}_3$, 9H, s) |
| 7 | —N⟨⟩NCH$_2$CH=CH$_2$ | amorphous | 0.29 | C | 1600 (C=O) | 3.66 (C$\underline{H}_2$NC$\underline{H}_2$, 4H, br) |
| 8 | —N⟨⟩NCH$_2$CH$_2$CH=CH$_2$ | prism | 0.33 | C | 1620 (C=O) | 3.70 (C$\underline{H}_2$NC$\underline{H}_2$, 4H, br) |
| 9 | —N⟨⟩NCH$_2$CH=C(CH$_3$)$_2$ | prism | 0.55 | B | 1618 (C=O) | 3.60 (C$\underline{H}_2$NC$\underline{H}_2$, 4H, br) |

TABLE 1-continued

| Derivative No. | A | Crystal form | TLC Rf | Solvent system* | IR spectrum (cm$^{-1}$) | Chemical shift of proton in amino group introduced** ($\delta$, ppm) |
|---|---|---|---|---|---|---|
| 10 | 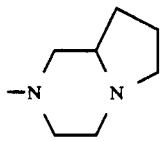 | amorphous | 0.55 | B | 1610 (C=O) | — |

(Notes)
*Solvent system
A: chloroform/methanol = 20/1 (v/v)
B: chloroform/methanol = 9/1 (v/v)
C: chloroform/acetone = 7/3 (v/v)
D: ethyl acetate
**Abbreviation
s: singlet, t: triplet, br: broad The rifamycin derivative (I) of the present invention shows a strong antibacterial activity against Gram-positive bacteria and acid-fast bacteria.

The antibacterial activity of the rifamycin derivative (I) of the present invention was determined according to the standard method of Japan Society of Chemotherapy [Chemotherapy (Tokyo), 29, 76 (1981)]. The results obtained with respect to the typical compounds are shown in Table 2. As shown in Table 2, the rifamycin derivative (I) of the present invention shows a strong antibacterial activity against Gram-positive bacteria and acid-fast bacteria Derivative No. in Table 2 corresponds to derivative No. in Table 1.

TABLE 2

| Test organism | Minimal inhibitory concentration ($\mu$g/ml) | | | | |
|---|---|---|---|---|---|
| | Derivative No. 1 | Derivative No. 2 | Derivative No. 3 | Derivative No. 4 | Derivative No. 5 |
| *Micrococcus luteus* IFO 12708 | 0.02≧ | 0.02≧ | 0.02≧ | 0.02≧ | 0.02≧ |
| *Bacillus subtilis* IFO 3134 | 0.02≧ | 0.04 | 0.02≧ | 0.02≧ | 0.16 |
| *Staphylococcus aureus* IFO 12732 | 0.02≧ | 0.02≧ | 0.02≧ | 0.02≧ | 0.02≧ |
| *Escherichia coli* IFO 12734 | >10 | >10 | >10 | >10 | >10 |
| *Klebsiella pneumoniae* IFO 3512 | >10 | >10 | >10 | >10 | >10 |
| *Mycobacterium smegmatis* ATCC 607 | 5 | 2.5 | 2.5 | 1.25 | 5 |

| Test organism | Minimal inhibitory concentration ($\mu$g/ml) | | | | | |
|---|---|---|---|---|---|---|
| | Derivative No. 6 | Derivative No. 7 | Derivative No. 8 | Derivative No. 9 | Derivative No. 10 | Rifampicin |
| *Micrococcus leteus* IFO 12708 | 0.02≧ | 0.02≧ | 0.02≧ | 0.02≧ | 0.02≧ | 0.02≧ |
| *Bacillus subtilis* IFO 3134 | 0.02≧ | 0.04 | 0.02≧ | 0.08 | 0.02≧ | 0.08 |
| *Staphylococcus aureus* IFO 12732 | 0.02≧ | 0.02≧ | 0.02≧ | 0.02≧ | 0.02≧ | 0.02≧ |
| *Escherichia coli* IFO 12734 | >10 | >10 | >10 | >10 | 10 | >10 |
| *Klebsiella pneumoniae* IFO 3512 | >10 | >10 | >10 | >10 | 10 | 5 |
| *Mycobacterium smegmatis* ATCC 607 | 1.25 | 2.5 | 2.5 | 2.5 | 2.5 | 10 |

The rifamycin derivative (I) of the present invention also exhibits a strong antibacterial activity against tubercle bacilli.

The antibacterial activity of the rifamycin derivative (I) against a tubercle bacillus was determined as follows: A tubercle bacillus, *Mycobacterium tuberculosis* H$_{37}$Rv, was cultured in the Dubos medium to prepare a suspension containing the bacterium in a concentration of 1 mg/ml. The suspension was diluted ten times with sterile distilled water and 0.05 ml of the dilution was inoculated into 2 ml of the Kirchner liquid medium containing 10% by volume of bovine serum. The evaluation of the antibacterial activity was carried out in a usual manner. Each test compound was diluted with the Kirchner liquid medium containing 10% by volume of bovine serum by a two-fold series. Then, the abovementioned medium containing the bacterium was added to each of the dilutions of the test compound. After each medium was cultured at 37° C. for 4 weeks, the growth of the test bacteria was observed by the naked eye. The minimum concentration of the test compound, at which the growth of the test bacterium was completely inhibited, was taken as minimal inhibitory concentration.

The results are shown in Table 3. From the results shown in Table 3, it is confirmed that the rifamycin derivative (I) of the present invention exhibits a strong antibacterial activity against tubercle bacilli. Derivative No. in Table 3 corresponds to derivative No. in Table 1.

TABLE 3

| Derivative No. | Minimal inhibitory concentration ($\mu$g/ml) |
|---|---|
| 1 | 0.035 |
| 2 | 0.017 |
| 3 | 0.017 |
| 4 | 0.017 |
| 5 | 0.07 |
| 6 | 0.008 |
| 7 | 0.035 |
| 8 | 0.017 |
| 9 | 0.035 |
| 10 | 0.15 |
| Rifampicin | 0.6 |

The rifamycin derivative (I) of the invention exhibits an excellent effect on a treatment of mice experimentally infected by oral administration.

A test for examining the therapeutic effect of the rifamycin derivative (I) on tuberculosis using mice are shown below.

Groups of 20 ddY male mice (5 weeks) were employed A tubercle bacillus, *Mycobacterium tuberculosis* H37Rv was cultured in the Dubos medium to obtain a concentrated suspension of the bacterium and 0.2 of the suspension (viable count: $2.4 \times 10^8$) was inoculated into the caudal vein of the mice to make them being infected with tuberculosis. There was prepared a suspension of each test compound in a 2.5% by weight aqueous solution of gum arabic containing 0.2% by weight Tween 80. The treatment was started on the next day of the infection. The suspension of the test compound was orally administered to the mice in a dose of 0.2 ml, i.e. 200 µg/mouse. As a control, a 2.5% by weight aqueous solution of gum arabic containing 0.2% by weight of Tween 80 which did not contain any test compound was administered to mice. The treatment was conducted once a day and six days a week. The therapeutic effect was evaluated on the basis of prolonged life of the mice being infected with tuberculosis.

The results are shown in FIG. 1. In FIG. 1, the point, a, means the time that mice were infected, and the point, b, means the time that the treatment started. From the results shown in FIG. 1, in the treatment using the derivative No. 2 of the invention, there was not observed any dead mouse for 38 days from the beginning of the treatment. Accordingly it is apparent that the derivative No. 2 exhibits an excellent therapeutic effect as compared with rifampicin as a comparative medicine and the derivative A disclosed in U.S. Pat. No. 4,690,919 having the formula mentioned below. On the other hand, as for the derivative B disclosed in U.S. Pat. No. 4,690,919, having the formula mentioned below, and the derivative C disclosed in EP No. 0253340, having the formula mentioned below, it is confirmed that they are inferior to rifampicin in their therapeutic effect in a therapeutic test.

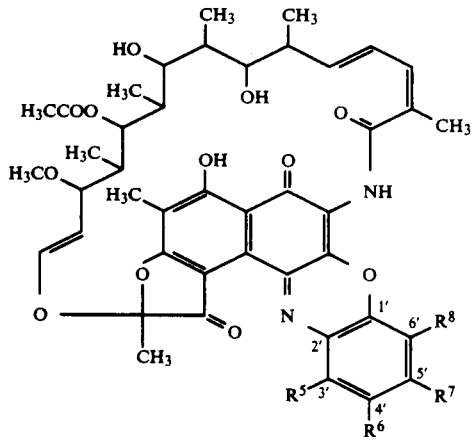

Derivative A: $R^5$: —OH, $R^6$ and $R^8$: —H, and

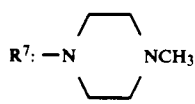

Derivative B: $R^5$, $R^6$ and $R^8$: —H, and $R^7$: —N 

Derivative C: $R^5$ and $R^6$: —H, $R^7$: —N , and $R^8$: —C$_2$H$_5$

Further, the above-mentioned test for treatment of mice being infected with tuberculosis was repeated except that groups of 10 ddY male mice were used to determine the survival rate of the mice on the fortieth day after the beginning of the test. The results are shown in Table 4 and Table 5.

TABLE 4

| Test compound | Survival rate (%) |
|---|---|
| Control (not given) | 30 |
| Derivative No. 2 | 100 |
| Derivative No. 3 | 100 |
| Derivative No. 5 | 100 |
| Derivative No. 7 | 100 |
| Derivative No. 9 | 100 |
| Derivative No. 10 | 100 |
| Rifampicin | 80 |

From the results shown in Table 4, as for the groups which were given the derivative No. 2, No. 3, No. 5, No. 7, No. 9 or No. 10 of the invention, there was not observed any dead mouse. On the other hand, the survival rate of the control group which was not given any medicine was 30%, and the survival rate of the group which was given rifampicin was 80%.

TABLE 5

| Test compound | Survival rate (%) |
|---|---|
| Control (not given) | 0 |
| Derivative No. 1 | 100 |
| Derivative No. 4 | 100 |
| Derivative No. 6 | 100 |
| Derivative No. 8 | 100 |
| Rifampicin | 40 |

From the results shown in Table 5, as for the groups which were given the derivative No. 1, No. 4, No. 6, or No. 8 of the invention, there was not observed any dead mouse. On the other hand, all mice died in the control group which was not given any medicine, and the survival rate of the group which was given rifampicin was 40%. The results show that the rifamycin derivative (I) of the invention is very effective as a drug for tuberculosis.

Further the rifamycin derivatives shown in Table 1 did not show any toxicity when they were orally administered in a dose of 1,000 mg/kg to mice. The results reveal that the rifamycin derivative (I) of the present invention has a low toxicity.

Antibacterial agents containing the rifamycin derivative (I) as an effective ingredient may be in any preparation form for oral, or rectal or other parenteral administration. Examples of the preparation form are, for instance, tablets, capsules, granules, syrups, suppositories, ointments, and the like. Carriers used for the preparations of the antibacterial agent of the present invention are organic or inorganic pharmaceutical carriers in either solid or liquid state, which are inactive under usual conditions, suitable for oral, or rectal or other parenteral administration. Examples of the carrier include crystalline cellulose, gelatin, lactose, starch, magnesium stearate, talc, vegetable or animal fats or oils, gums and polyalkylene glycol. The content of the rifamycin derivative (I) in the preparation varies from 0.2 to 100% by weight. The antibacterial agent of the present invention can contain another pharmaceutical ingredient such as another antibacterial agent compatible with the rifamycin derivative (I). In this case, the rifamycin derivative (I) is not necessarily a main ingredient of the preparation.

The antibacterial agent of the present invention is administered in such a dose that the desired activity is achieved without any side-effect. Though the actual dose should be determined according to the judgement of the doctor, a usual dosage is about 10 mg to about 10 g, preferably about 20 mg to about 5 g, on the basis of the rifamycin derivative (I) per day for adults. The antibacterial agent of the present invention can be used in a pharmaceutical dosage unit containing 1 mg to 5 g, preferably 3 mg to 1 g of an effective component.

The novel rifamycin derivative (I) according to the present invention has a strong antibacterial activity and excellent pharmacological characteristics.

The present invention is more specifically described and explained by the following Examples. However, it should be understood that the present invention is not limited to such Examples and various changes and modifications can be made without departing from the scope and spirit of the present invention.

In Examples, derivative No. corresponds to derivative No. in Table 1. The mixing ratio of solvents as an eluent used in column chromatography or as a developer used in thin layer chromatography was represented in terms of volume ratio (v/v).

EXAMPLE 1

Synthesis of derivative No. 1

After 8.0 g of 3'-hydroxybenzoxazinorifamycin prepared according to the process for disclosed in U.S. Pat. No. 4,690,919 was dissolved in 80 ml of dimethyl sulfoxide (hereinafter referred to as "DMSO"), a solution of 2.85 g of 1-n-butylpiperazine in 20 ml of DMSO was added thereto. To the solution was added 9.0 g of manganese dioxide, and the mixture was stirred at room temperature for 40 hours. After the reaction mixture was diluted by addition of 600 ml of ethyl acetate, manganese dioxide was filtered off. The filtrate was washed three times with a saturated aqueous solution of sodium chloride, and dried over anhydrous sodium sulfate. The solvent was distilled away under reduced pressure, and the residue was purified twice by silica-gel column-chromatography employing Wakogel ® C-200 [eluent: chloroform-acetone (4:1) for the first purification and chloroform-methanol (50:1) for the second purification]. Then, the product was crystallized from a mixture of ethyl acetate and n-hexane to give 3.58 g of the desired derivative No. 1.

EXAMPLE 2

Synthesis of derivative No. 2

After 3.0 g of 3'-hydroxybenzoxazinorifamycin was dissolved in 30 ml of DMSO, 1.05 g of 1-isobutylpiperazine and then 3.0 g of manganese dioxide were added thereto. The mixture was stirred at room temperature for 25 hours. To the reaction mixture was added 200 ml of ethyl acetate and manganese dioxide was filtered off. Then, the filtrate was washed successively with water and with a saturated aqueous solution of sodium chloride, and dried over anhydrous sodium sulfate overnight. The solvent was distilled away under reduced pressure, and the residue was purified by silica-gel column-chromatography employing Wakogel ® C-200 [eluent: chloroform-acetone (8:2)]. The product was crystallized from a mixture of ethyl acetate and n-hexane to give 0.82 g of the derivative No. 2.

EXAMPLE 3

Synthesis of derivative No. 3

After 6.0 g of 3'-hydroxybenzoxazinorifamycin was dissolved in 60 ml of DMSO, 2.13 g of 1-(cyclopropylmethyl)piperazine and then 6.0 g of manganese dioxide were added thereto. The mixture was stirred at room temperature for 30 hours. After the reaction mixture was treated in the same manner as in Example 2, the residue was purified three times by silica-gel column-chromatography employing Wakogel ® C-200 [eluent: chloroform-acetone (8:2)]to give 4.0 g of the derivative No. 3.

EXAMPLE 4

Synthesis of derivative No. 4

After 4.5 g of 3'-hydroxybenzoxazinorifamycin was dissolved in 45 ml of DMSO, 1.56 g of 1-sec butylpiperazine and then 4.5 g of manganese dioxide were added thereto. The mixture was stirred at room temperature for 22 hours. After the reaction mixture was treated in the same manner as in Example 2, the residue was purified twice by silica-gel column-chromatography employing Wakogel ® C-200 [eluent: chloroform-acetone (8:2) for the first purification and chloroform-methanol (98:2) for the second purification] to give 3.9 g of the derivative No. 4.

EXAMPLE 5

Synthesis of derivative No. 5

After 8.0 g of 3'-hydroxybenzoxazinorifamycin was dissolved in 80 ml of DMSO, a solution of 3.13 g of 1-isoamylpiperazine in 20 ml of DMSO was added thereto. To the solution was added 9.0 g of manganese dioxide, and the mixture was stirred at room temperature for 40 hours. After the reaction mixture was treated in the same manner as in Example 1, the residue was purified three times [eluent: chloroform-acetone (5:1) for the first purification, chloroform-ethyl acetate (2:1) for the second purification and chloroform-ethyl acetate-methanol (15:10:1) for the third purification], and the product was crystallized from a mixture of chloroform and n-hexane to give 3.38 g of the derivative No. 5.

EXAMPLE 6

Synthesis of derivative No. 6

10 After 4.38 g of 3'-hydroxybenzoxazinorifamycin was dissolved in 30 ml of DMSO, 3.10 g of 1-tert-butylpiperazine and 1.0 g of manganese dioxide were added thereto, and the mixture was stirred at room temperature for 21 hours. The reaction mixture was diluted with 50 ml of chloroform and insoluble substances were filtered off. The filtrate was washed successively with water and with a saturated aqueous solution of sodium chloride, and dried over anhydrous sodium sulfate. Chloroform was distilled away under reduced pressure, and the residue was purified by silica-gel column-chromatography employing Wakogel® C-200 [eluent: chloroform-methanol (98:2)]. The product was crystallized from a mixture of ethyl acetate and n-hexane to give 2.97 g of the desired derivative No. 6.

EXAMPLE 7

Synthesis of derivative No. 7

After 4.5 g of 3'-hydroxybenzoxazinorifamycin was dissolved in 40 ml of DMSO, 1.39 g of 1-allylpiperazine and then 4.5 g of manganese dioxide were added thereto. The mixture was stirred at room temperature for 25 hours. After the reaction mixture was treated in the same manner as in Example 6, the residue was purified four times by silica-gel column-chromatography employing Wakogel® C-200 [eluent: chloroform-methanol (95:5)]to give 2.7 g of the derivative No. 7.

EXAMPLE 8

Synthesis of derivative No. 8

After 4.5 g of 3'-hydroxybenzoxazinorifamycin was dissolved in 45 ml of DMSO, 2.0 g of 1-(3-butenyl)piperazine and then 4.5 g of manganese dioxide were added thereto. The mixture was stirred at room temperature for 23.5 hours. After 50 ml of chloroform was added to the reaction mixture, manganese dioxide was filtered off. The filtrate was washed successively with water and with a saturated aqueous solution of sodium chloride, and dried over anhydrous sodium sulfate overnight. Then, the solvent was distilled away under reduced pressure. The residue was purified twice by silica-gel column-chromatography employing Wakogel® C-200 [eluent: chloroform-acetone (8:2) for the first purification and chloroform-methanol (99:1) for the second purification], and the product was crystallized from a mixture of chloroform and n-hexane to give 3.36 g of the desired derivative No. 8.

EXAMPLE 9

Synthesis of derivative No. 9

After 4.5 g of 3'-hydroxybenzoxazinorifamycin was dissolved in 45 ml of DMSO, 1.69 g of 1-(3-methyl-2-butenyl)piperazine and then 4.5 g of manganese dioxide were added thereto. The mixture was stirred at room temperature for 28 hours. After the reaction mixture was treated in the same manner as in Example 2, the residue was purified twice by silica-gel column-chromatography employing Wakogel® C-200 [eluent: chloroform-methanol (98:2) for the first purification and ethyl acetate for the second purification], and the product was crystallized from a mixture of ethyl acetate and n-hexane to give 1.8 g of the derivative No. 9.

EXAMPLE 10

Synthesis of derivative No. 10

After 1.8 g of 3'-hydroxybenzoxazinorifamycin was dissolved in 18 ml of DMSO, 0.56 g of 1,4-diazabicyclo[4.3.0]nonane prepared according to the method proposed by M. E. Freed et al. [Journal of Organic Chemistry, 25, 2108(1960)]and then 1.8 g of manganese dioxide were added thereto. The mixture was stirred at room temperature for 52 hours.

The reaction mixture was treated in the same manner as in Example 2, and the residue was purified five times by silica-gel column-chromatography employing Wakogel® C-200 [eluent: chloroform-methanol (98:2)] to give 0.3 g of the derivative No. 10.

In addition to the ingredients used in the Examples, other ingredients can be used in the Examples as set forth in the specification to obtain substantially the same results.

What we claim is:

1. A rifamycin derivative having the formula (I):

[Structural formula of rifamycin derivative (I)]

wherein A is a group having the formula:

[piperazine structure: $-N\underset{\_\_\_}{\overset{\_\_\_}{\diagup\diagdown}}NR^1$]

in which
R$^1$ is an alkyl group having 4 or 5 carbon atoms or an alkenyl group having 3 to 5 carbon atoms, or a group having the formula:

[bicyclic structure with $(CH_2)_n$]

in which n is 3 or 4;
or a pharmaceutically acceptable salt thereof.

2. The rifamycin derivative or a pharmaceutically acceptable salt thereof of claim 1, wherein, in the formula (I), A is a group having the formula:

formula: $-N\underset{\_\_\_}{\overset{\_\_\_}{\diagup\diagdown}}NCH_2CH_2CH_2CH_3$.

3. The rifamyacin derivative or a pharmaceutically acceptable salt thereof of claim 1, wherein, in the formula (I), A is a group having the formula:

formula: $-N\underset{\_\_\_}{\overset{\_\_\_}{\diagup\diagdown}}NCH_2CH(CH_3)_2$.

4. The rifamycin derivative or a pharmaceutically acceptable salt thereof of claim 1, wherein, in the formula (I), A is a group having the formula:

formula: 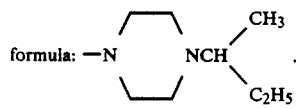

5. The rifamycin derivative or a pharmaceutically acceptable salt thereof of claim 1, wherein, in the formula (I), A is a group having the formula:

formula: 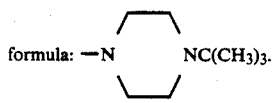

6. A process for preparing a rifamycin derivative having the formula (I):

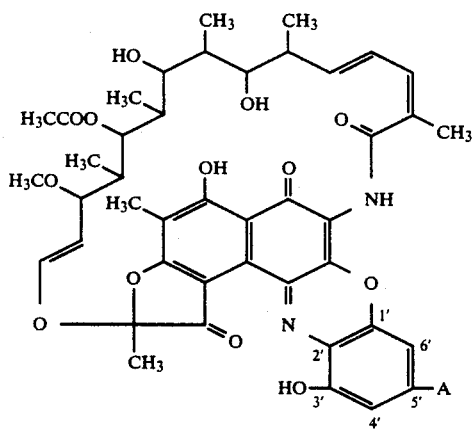

wherein A is a group having the formula:

in which
R[1] is an alkyl group having 4 or 5 carbon atoms or an alkenyl group having 3 to 5 carbon atoms, or a group
having the formula:

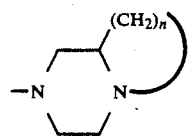

in which n is 3 or 4;
or a pharmaceutically acceptable salt thereof, the process comprising: reacting a rifamycin derivative having the formula (II):

(II)

[structure]

with an amine having the formula:

A—H wherein A is a group having the formula:

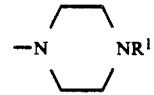

in which

R[1] is an alkyl group having 4 or 5 carbon atoms or an alkenyl group having 3 to 5 carbon atoms, or a group
having the formula:

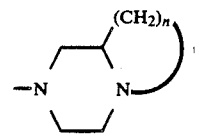

in which n is 3 or 4.

7. The process of claim 6, wherein said rifamycin derivative having the formula (II) is reacted with said amine having the formula: A—H wherein A is as defined above, in the presence of an oxidizing agent.

8. The process of claim 7, wherein said oxidizing agent is manganese dioxide.

9. An antibacterial composition comprising as an effective ingredient a rifamycin derivative having the formula (I):

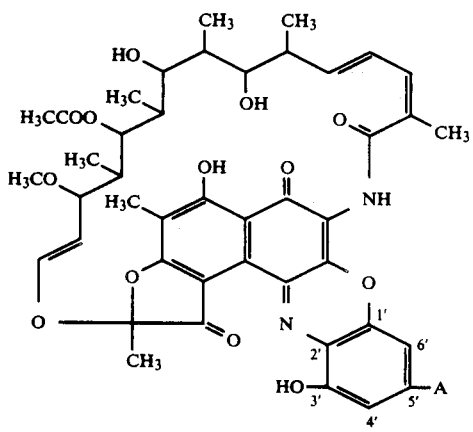 (I)
wherein A is a group having the formula:
$$-N\underset{\phantom{N}}{\overset{\phantom{N}}{\bigcirc}}NR^1$$
in which
R[1] is an alkyl group having 4 or 5 carbon atoms or an alkenyl group having 3 to 5 carbon atoms, or a group having the formula:
$$-N\underset{\phantom{N}}{\overset{(CH_2)_n}{\bigcirc}}N$$
in which n is 3 or 4;
or a pharmaceutically acceptable salt thereof.
* * * * *

UNITED STATES PATENT AND TRADEMARK OFFICE
CERTIFICATE OF CORRECTION

PATENT NO. : 4,983,602

DATED : January 8, 1991

INVENTOR(S) : Takehiko YAMANE, et al.

It is certified that error appears in the above-identified patent and that said Letters Patent is hereby corrected as shown below:

Column 4, line 10, change:

Column 5, line 1, change "ptoluenesulfonic acid" to read as -- p-toluenesulfonic acid --.

Column 9, line 65, change "abovementioned" to read as --above-mentioned--.

Column 11, line 2, change "ployed" to read as --ployed.--

Column 11, line 4, change "0.2" to --0.2 m$\ell$--.

Column 14, line 26, change "1-sec butylpiper-" to read as -- 1-sec-butylpiper- --.

Column 14, line 58, change "10 After 4.38 g" to read as --After 4.38 g--.

UNITED STATES PATENT AND TRADEMARK OFFICE
CERTIFICATE OF CORRECTION

PATENT NO. : 4,983,602
DATED : January 8, 1991
INVENTOR(S) : Takehiko Yamane, et al It is certified that error appears in the above-indentified patent and that said Letters Patent is hereby corrected as shown below:

Column 20, line 15, change:

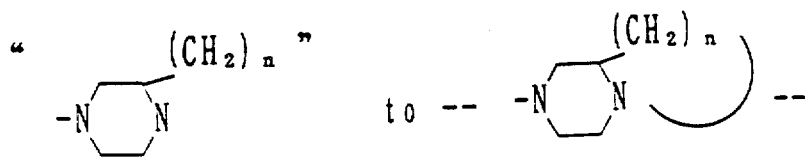

Signed and Sealed this

Twenty-second Day of March, 1994

Attest:

BRUCE LEHMAN

Attesting Officer

Commissioner of Patents and Trademarks